(12) United States Patent
Dreyer et al.

(10) Patent No.: US 8,359,109 B2
(45) Date of Patent: Jan. 22, 2013

(54) APPARATUS FOR DETERMINING AND/OR MONITORING A PROCESS VARIABLE

(75) Inventors: Volker Dreyer, Lörrach (DE); Udo Grittke, Steinen (DE); Kaj Uppenkamp, Wehr (DE); Franco Ferraro, Schwörstadt (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 627 days.

(21) Appl. No.: 12/226,662

(22) PCT Filed: Apr. 25, 2007

(86) PCT No.: PCT/EP2007/054053
§ 371 (c)(1),
(2), (4) Date: May 11, 2009

(87) PCT Pub. No.: WO2007/125067
PCT Pub. Date: Nov. 8, 2007

(65) Prior Publication Data
US 2009/0312846 A1    Dec. 17, 2009

(30) Foreign Application Priority Data
Apr. 28, 2006   (DE) .................. 10 2006 020 342

(51) Int. Cl.
*G05B 11/01*   (2006.01)
(52) U.S. Cl. ............... 700/11; 700/9; 713/323; 713/324
(58) Field of Classification Search ............... 700/9, 11, 700/19; 713/323, 324
See application file for complete search history.

(56) References Cited

U.S. PATENT DOCUMENTS

| 5,761,096 A | * | 6/1998 | Zakutin | 702/149 |
| 6,427,129 B1 | | 7/2002 | Lalla | |
| 2001/0006384 A1 | * | 7/2001 | Usaki | 345/204 |
| 2007/0028132 A1 | * | 2/2007 | Wang | 713/323 |

FOREIGN PATENT DOCUMENTS

| DE | 42 32 659 A1 | 3/1994 |
| DE | 42 39 954 A1 | 6/1994 |
| DE | 196 10 626 C2 | 9/1997 |
| DE | 197 30 158 A1 | 2/1999 |
| DE | 199 54 186 A1 | 5/2001 |
| DE | 100 56 353 A1 | 5/2002 |
| DE | 202 02 073 U1 | 7/2002 |
| EP | 0 892 249 A1 | 1/1999 |
| RU | 2 143 665 | 2/1999 |

(Continued)

*Primary Examiner* — Sean Shechtman
(74) *Attorney, Agent, or Firm* — Bacon & Thomas, PLLC

(57) ABSTRACT

An apparatus for determining and/or monitoring at least one process variable of a medium. The apparatus includes: at least one sensor unit for registering the process variable, wherein the sensor unit produces measurement signals; at least one electronics unit for controlling the sensor unit, wherein the electronics unit has at least one microprocessor; and at least one memory unit, which is associated with the sensor unit, and in which control data are storable. The control data specifically relate to the sensor unit and can be read out by the electronics unit. The microprocessor of the electronics unit is embodied in such a manner, that the microprocessor executes in an inactive state only basic functionalities, and that the microprocessor in an active state controls the sensor unit. The microprocessor transfers from the inactive state into the active state transfers by loading control data from the memory unit.

7 Claims, 1 Drawing Sheet

FOREIGN PATENT DOCUMENTS

| WO | WO 01/18502 | A1 | 3/2001 |
| WO | WO 02/17025 | A2 | 2/2002 |
| WO | WO 03/067021 | A2 | 8/2003 |
| WO | WO 2004/017025 | A1 | 2/2004 |
| WO | WO2004017025 | A1 | 2/2004 |

* cited by examiner

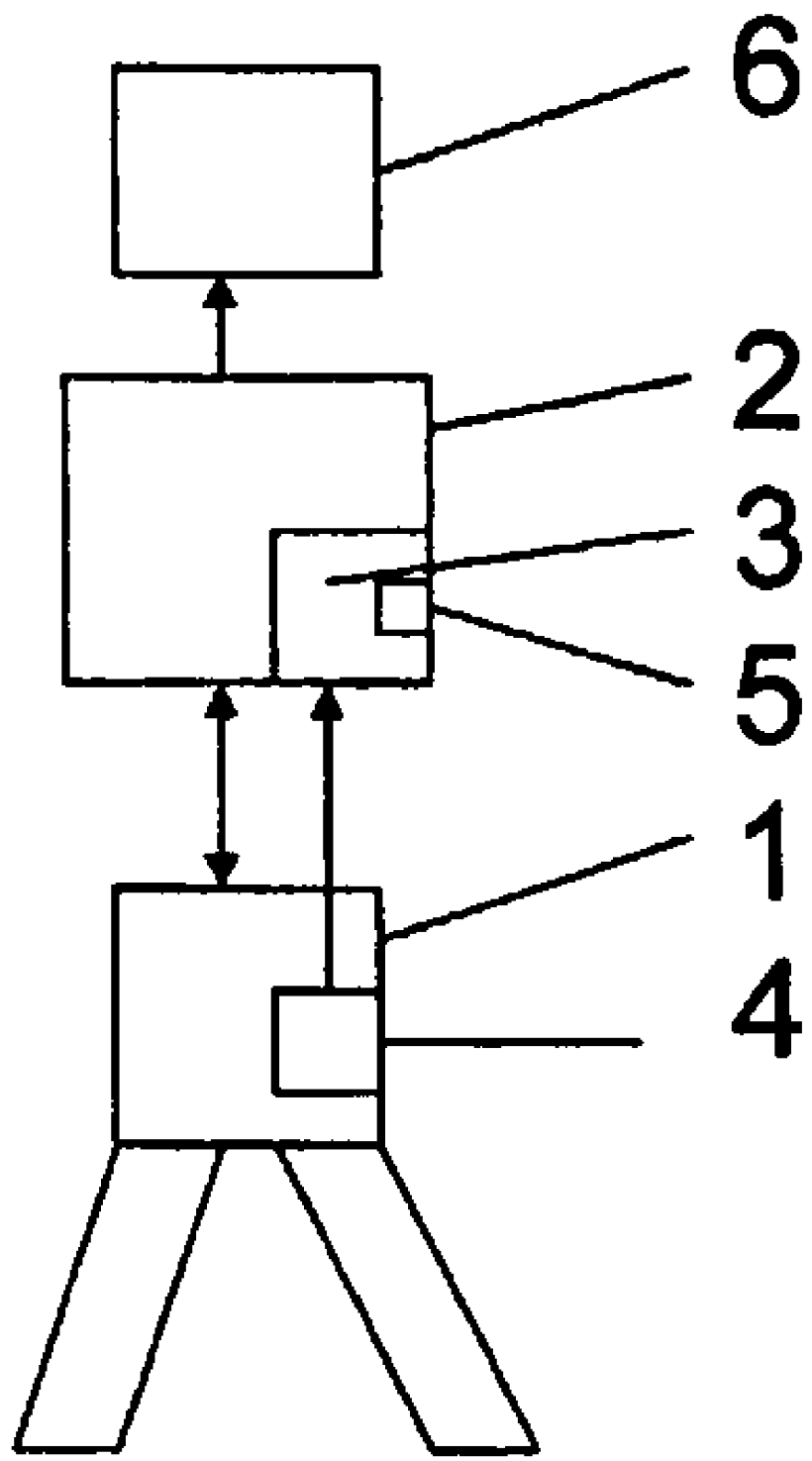

APPARATUS FOR DETERMINING AND/OR MONITORING A PROCESS VARIABLE

TECHNICAL FIELD

The invention relates to an apparatus for determining and/or monitoring at least one process variable of a medium. The apparatus includes: At least one sensor unit for registering the process variable, wherein the sensor unit produces measurement signals; at least one electronics unit for controlling the sensor unit, wherein the electronics unit has at least one microprocessor; and at least one memory unit, which is associated with the sensor unit, and in which control data are storable, wherein the control data specifically relate to the sensor unit and can be read out by the electronics unit. The process variable can be, for example, fill-level, density, viscosity, temperature, flow, pH-value or pressure. The medium is, for example, a liquid, a bulk good or a gas.

BACKGROUND DISCUSSION

In WO 01/18502 A1, a measuring apparatus is described, in which a fill-level is measured via the travel-time method. I.e., a measurement signal is radiated in the direction of the surface of a medium and, after interacting with the medium, received back. From the time difference, the fill-level can be ascertained. Suited as measurement signals are: Microwave signals, which are either freely radiated or guided on an electrical conductor; or also ultrasonic wave signals. The kind of measurement signals determines the kind of sensor unit required. At the same time, however, the evaluation in the case of sensors in the travel-time method is, in each case, identical. Therefore, in the measuring device of this WO 01/18502 A1, an evaluating unit is combined with different sensor units, in that the units common to the different sensor types are clustered and the specific components are connected with the sensor units. Basically, evaluating units of different measuring devices are coalesced to one evaluating unit, which is connectable with different sensor units.

For detecting a limit level of a medium, so-called oscillatory forks are known. The oscillations of these forks are evaluated as regards frequency, amplitude or phase. Exploited, for example, is the fact that the oscillation frequency decreases, when the medium covers the fork. In order to reliably recognize the reaching of a limit level, the so-called air-frequency must be known, thus the frequency, with which the fork oscillates freely and uncovered. This resonance frequency is, however, dependent on the particular construction of the fork—thus, even the resonance frequencies of the individual forks of a batch can differ. In order, nevertheless, to be able to switch reliably, the measuring devices are, therefore, equipped with a characterizing resistor or some characterizing element, e.g. an EEPROM, in which, for example, the resonance frequency of the oscillatory fork is stored. See, for example, DE 42 32 659 or DE 100 56 353 A1.

General technical development is moving ever further in the direction of modularizing and platform building. In such case, it must, however, always still be remembered, that a large number of measuring devices also serve the safety of a process plant; i.e., it must be assured, that such measuring devices function also safely and reliably. Especially, in the case of different modules, attention must be paid that the right components are connected with one another. This is especially true, when software programs or software components are involved.

SUMMARY OF THE INVENTION

An object of the invention is, therefore, to provide a modular measuring device, which has a high measure of safety of functioning.

The object is achieved by the invention by the features, that the microprocessor of the electronics unit is embodied in such a manner, that the microprocessor executes only basic functionalities in an inactive state, and that the microprocessor, in an active state, controls the sensor unit, wherein the microprocessor transfers from the inactive state into the active state by loading control data from a memory unit. The measuring device of the invention operates, thus, on the basis of a sensor unit associated with a memory unit. The control, or generally, the operating, of the sensor unit is performed by an electronics unit. In the electronics unit is located a microprocessor, which performs the actual controlling in the electronics unit. The microprocessor controls the sensor unit only when it has entered the active state by loading data out of the memory unit and, thus, has suitable data or programs, or program parts, for proper functioning. This activating—activating refers to the activating of the measuring procedure, i.e. to the operation of the sensor unit—can, in such case, occur upon first start-up of the measuring device, or, for example, after every, on occasion, new supplying of energy to the measuring device, or as a result of a special control command.

An embodiment provides, that the electronics unit is embodied in such a manner, that at least two different sensor units are controllable by the electronics unit, wherein the sensor units differ, in that they measure different process variables and/or apply different measuring principles. In this embodiment, the electronics unit can, thus, be coupled with different sensor units. This means, that the electronics unit also has the functionalities and options required for each case. As a function of the data of the memory unit associated with a sensor unit of interest, then the microprocessor of the electronics unit works in such a manner, that the sensor unit is suitably activated or the output signals are suitably evaluated. The invention permits, thus, that each sensor unit provides the parameters or programs required for its control or evaluation. In an embodiment, the sensor units are, in each case, a mechanically oscillatable unit—thus, for example, an oscillatory fork, or a single-rod oscillator, having an associated transducer unit transducing between mechanical oscillations and electrical signal (e.g. a piezoelectric element). The sensor units differ, however, in their application, which concerns either liquids or bulk goods. In the case of liquids, often the oscillation frequency is applied for determining and/or monitoring fill level, while, in the case of bulk goods, it is the amplitude. Correspondingly different are the exciting and evaluation of the signals. A further distinguishing feature lies in the kind of application, wherein, for example, a phase between the received and exciting signal is set, which, in the case of liquids, permits foam detection, or masks foam, as the case may be. I.e., the sensor units are controlled and embodied to have different sensitivities. Furthermore, one oscillatory unit can be applied for monitoring fill level, while another is applied for measuring density. Thus, the sensor units use the same measuring principle, while the application is, however, different and involves either different media or different process variables. In an additional embodiment, in one sensor unit, the vibronic measuring principle is utilized, while, in the case of a second sensor unit, it is, however, a capacitive measuring unit. In the case of both sensor units, each is supplied with an electrical signal, an alternating voltage, which differs, however, especially as regards frequency. Received by the sensor unit, in each case, is a measurement signal, which in the one case contains the information via the mechanical oscillations and in the other case via the capacitance of the arrangement composed of probe unit and wall of the container, or a second probe unit, and the medium as dielectric. The data of the memory unit give, thus, information concerning the different amplitude-, frequency- and/or phase ranges or concerning the pertinent signal form of the exciting signal, which are/is applied for each of the sensor units. The more digital technology is used for controlling the sensor unit or evaluating the data, the more sensor types can be encompassed.

An embodiment includes, that the electronics unit is embodied in such a manner, that stored in it are control programs for different sensor units and/or different measuring principles, and that the control data effects the activating of the control program suitable for sensor unit of interest. In this embodiment, stored in the electronics unit are the control programs necessary for different sensor units, i.e. the electronics unit is suited, in principle, for different sensor types. The data of the memory unit effect, that, in each case, the suitable program is executed.

An embodiment provides, that the control data includes a control program, which is specifically for control of the sensor unit, or that the control data includes program parts of a control program, which are specifically for the sensor unit. In this embodiment, located in the memory unit is/are the complete control program or sensor-specific components. Therewith, then, either the entire control program or the specific components is/are loaded into the electronics unit for controlling the sensor unit.

An embodiment includes, that the electronics unit is embodied in such a manner, that the electronics unit reads the control data out of the memory unit after receiving an activation command and/or after the establishing of a connection between the electronics unit and the sensor unit. In an embodiment, there is stored in the memory unit an identifier, or code, which is detected by the microprocessor in the case of a return of the voltage, i.e. in the case of turn-on or turning back on. If the pertinent control program or the required data is/are not yet in the microprocessor, then a loading of the program or the data is performed.

An embodiment provides, that the microprocessor of the electronics unit has at least one interface for updating the control program.

An embodiment includes, that the memory unit includes at least one code, which permits a specific association of the memory unit to the sensor unit.

BRIEF DESCRIPTION OF THE DRAWINGS

The invention will now be explained in greater detail on the basis of the appended drawing, the sole FIGURE of which shows as follows:

FIG. 1 a schematic drawing of a measuring apparatus of the invention.

DETAILED DISCUSSION

FIG. 1 shows a measuring device of the invention. The sensor unit 1 is, in this case, embodied in the form of a vibronic measuring device, wherein two oscillatory units of an oscillatory fork are secured on a membrane, or diaphragm, which is excited to execute mechanical oscillations. The characterizing variables of the oscillations, such as frequency, amplitude and phase, permit the ascertaining of such process variables as fill-level, density or viscosity. Sensor unit 1 is connected with an electronics unit 2, which supplies the sensor unit 1 with an electrical, alternating voltage, and which, in turn, receives an alternating voltage resulting, for example, via a piezo-electrical element, from the oscillations of the membrane, or diaphragm, or the two fork tines. This alternating voltage is then evaluated in the electronics unit 2 with respect to the required characterizing variables, phase-shifted and fed, amplified, back to the sensor unit 1.

The electronics unit 2 is, in such case, controlled by a microprocessor 3, which specifies, for example, the phase required to be set for the exciting signal and specifies also the kind of evaluation. For example, in the case of liquids, the frequency of the oscillations is evaluated, and, in the case of bulk goods, the amplitude. For these applications, also the sensor units 1 themselves differ, most often, as regards their construction, with the oscillatory units for bulk goods being, usually, larger and more robust than is the case for liquids. The kind of evaluation and/or the phase to be set are/is, here, stored in the memory unit 4, which is fixedly connected with the sensor unit 1. Memory unit 4 is, in such case, a data memory in the classic sense or also a microprocessor. The sensor unit 1 provides the needed data or, in an additional embodiment, the entire control program or the program parts required for the particular sensor unit 1, to the microprocessor 3. I.e., via the memory unit 4, an ordinary electronics unit 2 is turned into an electronics unit 2 specific and suitable for the sensor unit 1. Since the sensor unit 1 is, moreover, connected directly with the memory unit 4 and, thus, with its own data, it is assured, that always the right operating of the sensor unit 1 occurs.

The electronics unit 2 is, moreover, embodied in such a manner, that also other sensor units 1 can be connected and operated, which differ from one another in construction (e.g. oscillatory fork for a liquid or for a bulk good, or single-rod oscillator, instead of a fork) or in the measuring principle used. Thus, it is, on the one hand, possible to make, with one electronics unit 2, different measuring devices with, in each case, different sensor units 1. On the other hand, also, the electronics unit 2 can be replaced, without having to de-install e.g. the entire measuring device, i.e. the sensor unit 1 can, for example, remain installed in the container and, on the side facing away from the process, only the electronics is exchanged. The essential data remain, in such case, in the sensor unit 1. Since, furthermore, each sensor unit 1 contains its control program or its relevant and specific parts, it is also assured, that the sensor unit 1 is operated with the right method suitable for it.

The measurement data, or the evaluated data, i.e. the certain process variables, are, here, displayed directly at the measuring location via a display unit 6. The required presentation data, e.g. the graphics driver, can likewise be stored in the memory unit 4.

Furthermore, also provided, here, is an interface 5, via which an update of the software is possible. An update of the control data in the sensor unit 1 can be implemented, for example, via an accessing of the memory unit 4.

The measuring device of the invention is distinguished, thus, by the fact, that, for example, a sensor unit 1 is connectable with different electronic units 2, and that the individual electronic units 2, in each case, read out from the memory unit 4 of the sensor unit the programs or program parts or program data relevant for the control the sensor unit 1. Thus, for example, a replacement of the electronics unit 2 is very easily possible, without having to remove the sensor unit 1 from the process, and, moreover, it is assured, that the sensor unit 1 is operated with the right program. Furthermore, different sensor units 1 can be connected to an electronics unit 2, and, also here, safety in the application is always assured by the invention.

The invention claimed is:

1. A modular measuring apparatus for determining and/or monitoring at least one process variable of a liquid, a bulk good or a gas, comprising:
   a sensor unit for installation in a container and for registering the process variable, wherein the sensor unit produces measurement signals;
   a replaceable electronics unit for operating and for controlling an operation of said sensor unit, wherein said electronics unit is connectable with said sensor unit and installable on a side of the container facing away from the process and wherein said electronics unit contains at least one microprocessor; and
   at least one memory unit associated with said sensor unit, which is fixedly connected with said sensor unit, and in which control data are stored such that said sensor unit provides the parameters or programs required for its control and evaluation, wherein:
   said control data relate specifically to the control of said sensor unit, and to evaluation of said measuring signals, and are readable by said electronics unit;
   said microprocessor of said electronics unit is embodied in such a manner, that said microprocessor executes only basic functionalities which do not concern the controlling of said sensor unit in an inactive state, and supplies said sensor unit with an electrical alternating voltage and controls a measuring procedure in an active state; and
   said microprocessor transfers from the inactive state into the active state by loading said control data from said memory unit.

2. The apparatus as claimed in claim 1, wherein:
   said electronics unit is embodied in such a manner, that at least two different sensor units are alternatively to one another connectable with and controllable by said electronics unit; and
   said two different sensor units differ, in that they measure different process variables and/or apply different measuring principles.

3. The apparatus as claimed in claim 1, wherein:
   said electronics unit is embodied in such a manner, that, present in it, are control programs for different sensor units and/or different measuring principles; and
   said control data effect activating of a control program suitable for a particular sensor unit.

4. The apparatus as claimed in claim 1, wherein:
   the control data include a control program, which is specifically for controlling said sensor unit, or the control data include parts of a control program, which are specifically for said sensor unit.

5. The apparatus as claimed in claim 1, wherein:
   said electronics unit is embodied in such a manner, that said electronics unit, after receiving an activation command and/or after establishing of a connection between said electronics unit and said sensor unit, reads said control data out of said memory unit.

6. The apparatus as claimed in claim 4, wherein:
   said microprocessor of said electronics unit has at least one interface for updating the control program.

7. The apparatus as claimed in claim 1, wherein:
   said memory unit includes at least one code permitting a specific association of said memory unit to said sensor unit.

\* \* \* \* \*